United States Patent
Hilden et al.

(10) Patent No.: US 6,753,433 B2
(45) Date of Patent: Jun. 22, 2004

(54) PROCESS FOR THE PREPARATION OF 1-(3-DIMETHYLAMINOPROPYL)-1-(4-FLUOROPHENYL)-1,3-DIHYDROISOBENZOFURAN-5-CARBONITRILE

(75) Inventors: Leif Hilden, Kauniainen (FI); Tuomas Huuhtanen, Tampere (FI); Petteri Rummakko, Espoo (FI); Arne Grumann, Kauniainen (FI); Pekka Pietikaeinen, Espoo (FI)

(73) Assignee: Orion Corporation, FERMION, Espoo (FI)

( * ) Notice: Subject to any disclaimer, the term of this patent is extended or adjusted under 35 U.S.C. 154(b) by 108 days.

(21) Appl. No.: 10/370,464

(22) Filed: Feb. 24, 2003

(65) Prior Publication Data

US 2003/0130527 A1 Jul. 10, 2003

Related U.S. Application Data

(62) Division of application No. 10/058,794, filed on Jan. 30, 2002.
(60) Provisional application No. 60/265,588, filed on Feb. 2, 2001.

(30) Foreign Application Priority Data

Jan. 30, 2001 (FI) .......................................... FI 20010175

(51) Int. Cl.$^7$ ...................... C07D 307/78; C07D 255/49
(52) U.S. Cl. .................. 549/467; 549/469; 558/415
(58) Field of Search ................. 549/467, 469; 558/415

(56) References Cited

U.S. PATENT DOCUMENTS

| | | |
|---|---|---|
| 4,136,193 A | 1/1979 | Bogeso et al. |
| 4,650,884 A | 3/1987 | Bogeso |
| 4,943,590 A | 7/1990 | Boegesoe et al. |
| RE34,712 E | 8/1994 | Boegesoe et al. |
| 6,229,026 B1 | 5/2001 | Petersen |
| 6,258,842 B1 | 7/2001 | Petersen et al. |
| 6,291,689 B1 | 9/2001 | Petersen et al. |
| 6,579,993 B2 | 6/2003 | Hilden et al. |

FOREIGN PATENT DOCUMENTS

| | | |
|---|---|---|
| EP | 0 171 943 | 2/1986 |
| EP | 1 015 416 | 5/1998 |
| EP | 1 123 284 | 4/2000 |
| EP | 1 042 310 | 7/2001 |
| EP | 1 032 566 | 9/2001 |
| FI | 98627 | 4/1997 |
| WO | WO 98/19511 | 5/1998 |
| WO | WO 98/19512 | 5/1998 |
| WO | WO 98/19513 | 5/1998 |
| WO | WO 99/30548 | 6/1999 |
| WO | WO 00/11926 | 3/2000 |
| WO | WO 00/12044 | 3/2000 |
| WO | WO 00/13648 | 3/2000 |
| WO | WO 00/23431 | 4/2000 |
| WO | WO 01/02383 | 1/2001 |

Primary Examiner—Joseph K. McKane
Assistant Examiner—Golam M M Shameem
(74) Attorney, Agent, or Firm—Oblon, Spivak, McClelland, Maier & Neustadt, P.C.

(57) ABSTRACT

Method for the preparation of 1-(3-dimethylaminopropyl)-1-(4-fluorophenyl)-1,3-dihydroisobenzofuran-5-carbonitrile (citalopram) comprising the reaction of a compound of formula

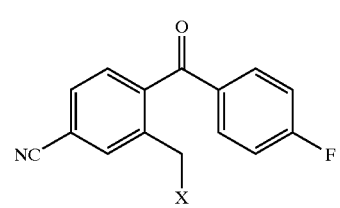

wherein X is a halogen, with organometallic dimethylaminopropyl halide. Other aspects of the invention are new compounds of formula II and formula III and their preparation.

10 Claims, No Drawings

PROCESS FOR THE PREPARATION OF 1-(3-DIMETHYLAMINOPROPYL)-1-(4-FLUOROPHENYL)-1,3-DIHYDROISOBENZOFURAN-5-CARBONITRILE

This application is a division f U.S. patent application Ser. No. 10/058,794, which was filed on Jan. 30, 2002, now U.S. Pat No. 6,579,993 and claims priority to U.S. Provisional Application No. 60/265,588, which was filed on Feb. 2, 2001.

CROSS REFERENCES TO RELATED APPLICATIONS

This application claims priority to U.S. Provisional Patent Application No. 60/265,588, filed on Feb. 2, 2001, and Finnish Patent Application No. FI20010175, filed on Jan. 30, 2001, both of which are incorporated herein by reference in their entireties.

BACKGROUND OF THE INVENTION

1. Field of the Invention

The present invention relates to a novel process for the preparation of 1-(3-dimethylaminopropyl)-1-(4-fluorophenyl)-1,3-dihydroisobenzofuran-5-carbonitrile, which is a well known antidepressant, citalopram.

2. Discussion of the Background

Citalopram is a selective, centrally acting serotonin (5-hydroxytryptamine; 5HT) reuptake inhibitor having antidepressant activity. This activity has been described, e.g., in J. Hyttel, Prog. Neuro-Psychopharmacol. & Biol. Psychiat., 1982, 6, 277–295 and A. Gravem, Acta Psychiatr. Scand., 1987, 75, 478–486. In EP-A 474 580 it has been disclosed that citalopram is also effective in the treatment of dementia and cerebrovascular disorders.

Citalopram has the following structure:

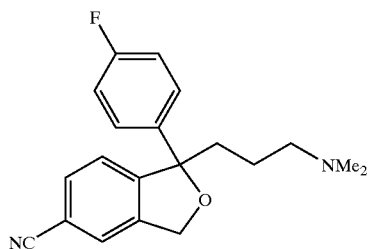

I

Citalopram was first described in DE 2,657,013 corresponding to U.S. Pat. No. 4,136,193. It was prepared by the reaction of 1-(4-fluorophenyl)-1,3-dihydro-5-isobenzofurancarbonitrile with a 3-(N,N-dimethylamino) propyl halide in the presence of a condensing agent. The starting material was prepared from the corresponding 5-bromo derivative by a reaction with cuprous cyanide. The other outlined reaction, in general terms, comprises the ring closure of the 5-bromo dihydroxy compound of formula IV

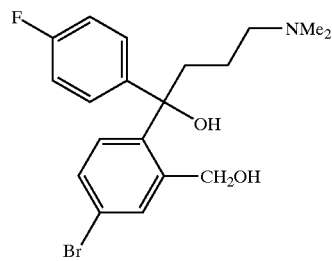

IV in the presence of a dehydrating agent. After the ring closure, the 5-bromo group is replaced by a cyano group using cuprous cyanide. The starting material for the compound of formula IV is obtained from 5-bromophthalide by two successive Grignard reactions.

Another preparation process is described in U.S. Pat. No. 4,650,884. In that process the ring closure of the dihydroxy compound of formula V

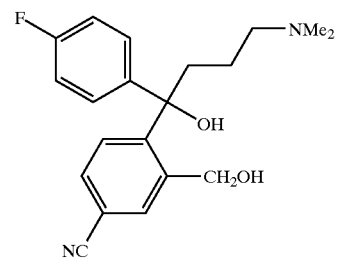

V is achieved by dehydration with strong sulfuric acid. The starting material is prepared from 5-cyanophthalide by two successive Grignard reactions.

Other processes for the preparation of citalopram are disclosed in patent applications WO 98/19511, WO 98/19512, WO 98/19513, WO 99/30548, WO 00/12044, WO 00/13648, and WO 00/23431. In U.S. Pat. No. 4,943,590, preparation methods for individual enantiomers of citalopram are disclosed. In the process described, the dihydroxy compound of formula V is first transformed into an ester and ring closure is then achieved in the presence of a base.

In the process described in WO 2000/12044 ring closure of a compound of formula VI

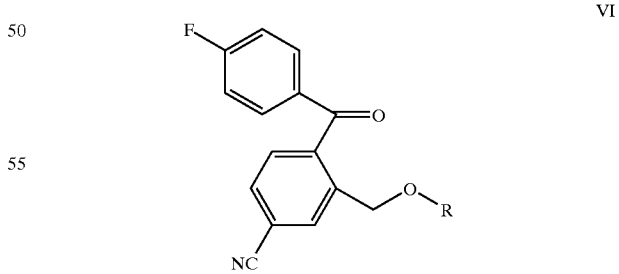

VI takes place spontaneously after a reaction with 3-(N,N,-dimethylamino)-propyl magnesium halide. Three different ways to prepare compound VI are described. One of the methods includes protection of (4-cyano-2-hydroxymethylphenyl)-4-fluorophenyl methanol followed by an oxidation to afford compounds of formula VI. The starting hydroxymethyl alcohol compound can be obtained from a phthalide compound by a Grignard reaction followed by the reduction of the resulting ketone. Another method comprises the reaction of 5-cyanophthalide with 4-fluoromagnesiumhalide followed by the the reaction with R-X, wherein R is $C_{1-6}$ alkyl, acyl, alkylsulfonyl ar arylsulfonyl and X is a leaving group, to afford compound VI. In the reaction of 5-cyanophthalide, the resulting ketone compound can also react with the Grignard reagent used, and undesirable side products are formed. It is also possible that the product forms a cyclic hemiketal which does not react in the following step. The third preparation method for compound VI described in WO 00/12044 can be used for the preparation of the S-enantiomer of citalopram.

SUMMARY OF THE INVENTION

The present invention provides novel processes for the preparation of citalopram comprising halogenation of 5-cyanophthalide to afford an acid halogenide compound of formula II wherein X is a halogen, and threafter obtaining citalopram through two successive reactions with suitable organometallic halides or organoboranes according to scheme 1.

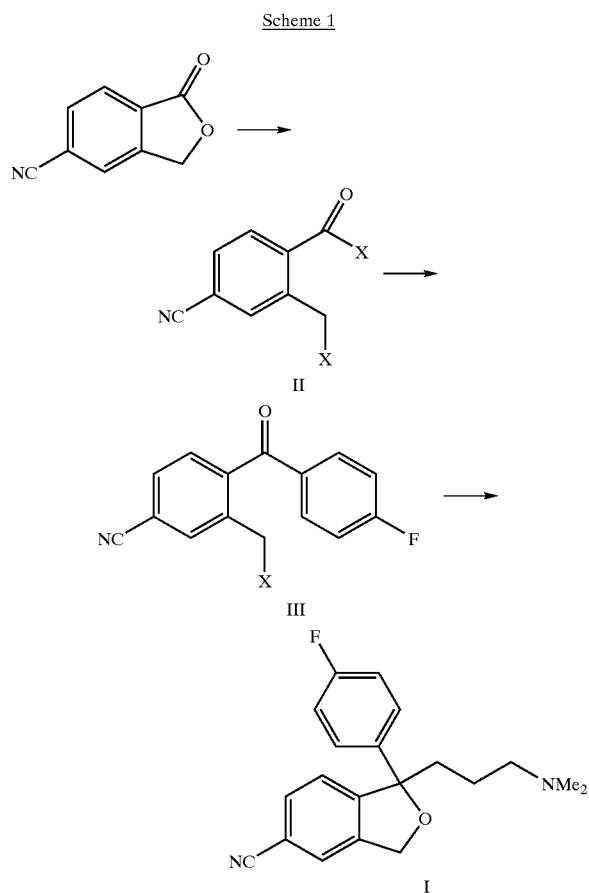

The process comprises:

a) halogenation of 5-cyanophthalide, thereby obtaining a compound of formula II

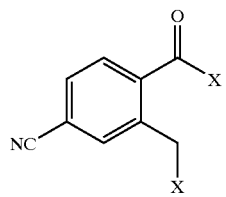

wherein X is halogen, b) the reaction of a compound of formula II with an organometallic 4-fluorophenyl halide or 4-fluorophenylborane to afford a compound of formula III

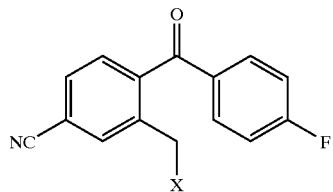

wherein X is as defined above, and c) the reaction of a compound of formula III with an organometallic dimethylaminopropyl halide to afford 1-(3-dimethylamino-propyl)-1-(4-fluorophenyl)-1,3-dihydroisobenzofuran-5-carbonitrile (citalopram), which is isolated as the base or a pharmaceutically acceptable salt thereof.

Formation of the halide compound of formula II serves two ends. First, high selectivity of the following reaction is obtained, and second, a leaving group in the benzylic position is introduced, so that ring closure to citalopram occurs spontaneously after treatment with a second Grignard reagent.

The resulting citalopram may be isolated as the base or a pharmaceutically acceptable salt thereof.

Another aspect of the present invention are novel intermediate compounds of formula II and III wherein X is a halogen, preferably chloro or bromo, most preferably chloro.

Still other aspects of the invention are processes for the preparation of said intermediates of formula II and III.

Yet another aspect of the invention relates to an antidepressant pharmaceutical composition comprising citalopram or its pharmaceutically acceptable acid addition salts prepared by the process of the invention.

In the context of the present invention, halogen means chloro, bromo, iodo, or fluoro.

The process of the present invention from 5-cyanophthalide to citalopram via acid halogenide is not described in any of the patents mentioned or in any other publication known.

DETAILED DESCRIPTION OF THE PREFERRED EMBODIMENTS

Surprisingly, it has been found that if 5-cyanophthalide is halogenated, the reaction of the resulting compound of formula II with an organometallic 4-fluorohalide or with a 4-fluorophenyl borane is very selective and the subsequent reaction of a compound of formula III with an organometallic 3-dimethylaminopropyl halide gives citalopram in good yield and purity.

The first step of the process is the halogenation of 1-oxo-1,3-dihydro-isobenzofuran-5-carbonitrile (5-cyanophthalide) to form the compound of formula II where X is halogen, preferably chloro or bromo, most preferably chloro.

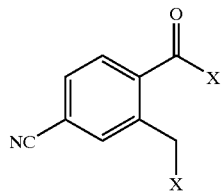

II

The halogenation can be performed by any suitable method known in the art, e.g, by the reaction with thionyl chloride in the presence of a suitable Lewis acid catalyst and a phase transfer catalyst. Catalysis by N,N-dimethylformamide (DMF) is also possible. Suitable Lewis acid catalysts are, e.g., $MgCl_2$, $MgBr_2$, $SnCl_2$, $SnCl_4$, $ZnCl_2$, $TiCl_4$, $AlCl_3$, $FeCl_3$, $BF_3Et_2O$, $BF_3$, $BBr_3$, $BCl_3$, $B(OEt)_3$, $B(OMe)_3$, $B(O-iPr)_3$. Preferably a boron-based Lewis acid catalyst is used. The types of phase transfer catalyst which can be used include halides of aromatic or aliphatic ammonium salts, for example tetramethylammonium chloride, tetrabutylammonium chloride or benzyl triethylammonium chloride, or phosphonium salts, for example butyltriphenylphosphonium chloride or tetraphenylphosphonium chloride. The catalysts are used in an amount of from 0.1 to 20 mol % each, preferably 0.5 to 10 mol %, based on the moles of 5-cyanophthalide. The reaction with the catalysts can be performed without any solvent, but if a solvent is used, any inert, high boiling solvent such as toluene, xylene, chlorobenzene or dichlorobenzene can be used.

The halogenation reagent used can be any suitable reagent used for halogenation, e.g. thionyl chloride, $PCl_3$, $PCl_5$, $CCl_4$ in triphenyl phosphine, oxalyl chloride, or cyanuric chloride in trialkyl amine.

The reagents for preparing the corresponding bromo compound can be, e.g., $PBr_3$, $PBr_5$, $PPh_3Br_2$, thionyl bromide, or oxalyl bromide.

The halogenation reagent is used in an amount of from 0.5 to 1000 equivalents (based on cyanophthalide), preferably 1 to 10 equivalents, most preferably 1 to 5 equivalents. The reaction temperature can be from 20 to 150° C. or reflux temperature, preferably 80 to 140° C., most preferably 100 to 130° C. The reaction time is from 0.5 to 15 hours, preferably less than 3 hours.

The reaction will be completed readily, and the conversion is close to 100%. The product can be isolated and purified by suitable methods known in the art or the following step can be performed without purification of compound II. The starting material, 5-cyanophthalide, can be prepared, e.g., as described in Tirouflet, Bull. Soc. Sci. Bretagne, 26, 1951, 35–46.

The advantage of making the acid halogenide is that the subsequent reaction with an organometallic 4-fluorophenyl halide or with 4-fluorophenyl borane is very selective unlike the reaction of the lactone directly with 4-fluorophenylmagnesium halide, where the resulting ketone compound is more reactive than the lactone and undesirable side products are formed.

The second step comprises the reaction of the halide compound of formula II with an organometallic or organoboron reagent to afford the compound of formula III.

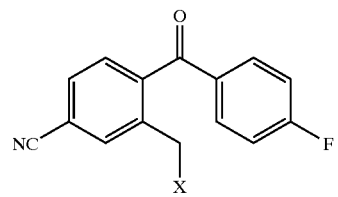

III

The reagent used is a 4-fluorophenylborane or an organometallic 4-fluorophenyl halide, wherein the metallic component can be Mg, Li, Cu, or Zn, preferably Mg or Cu. Preferably the reagent is a 4-fluorophenylmagnesium halide or a Grignard reagent of a 1-halide substituted 4-fluorobenzene, wherein the halogen component is preferably Cl or Br. Most preferably 4-fluorophenylmagnesium bromide is used. The amount of the reagent used is from 0.5 to 2.5 equivalents, preferably from 1 to 1.5 equivalents, based on the equivalents of the compound of formula II.

The reaction is carried out in an inert organic solvent such as toluene, xylene or commonly used ethers such as tetrahydrofuran, diethylether, di-n-butylether, tetrabutylmethyl ether, ethylene glycol dimethyl ether, 1,4-dioxane or mixtures thereof. The preferred solvents are tetrahydrofuran and ethylene glycol dimethyl ether or their mixtures with toluene. Cu, Ni, Pd, Ti, Fe, or Zn compounds can be used as catalysts. Preferably the reaction is performed without any catalyst. The reaction temperature is –80 to 60° C., preferably –20 to 20° C. The reaction is selective, and the resulting 4-(4-fluorobenzoyl)-2-halomethyl benzonitrile can be isolated and purified by crystallization or any other suitable method known in the art. The subsequent reaction can also be performed without isolation of the intermediate of formula III.

The final step is the reaction of the compound III with an organometallic 3-dimethylaminopropyl halide whereafter the ring closes spontaneously to afford citalopram. The metallo component of the organometallic 3-dimethylaminopropyl halide reagent used can be Mg, Li, Cu, or Zn, preferably Mg or Cu, most prefeeably Mg. Preferably the reagent is a Grignard reagent of a 3-(N,N-dimethylamino)propyl halide, wherein the halide is Cl or Br. Most preferably the reagent is 3-(N,N-dimethylamino) propylmagnesium chloride. The reaction is carried out in an inert organic solvent such as toluene, xylene or commonly used ethers such as tetrahydrofuran, diethylether, di-n-butylether, tetrabutylmethyl ether, ethylene glycol dimethyl ether or 1,4-dioxane or mixtures thereof. The preferred solvents are tetrahydrofuran or ethylene glycol dimethyl ether or their mixtures with toluene. Cu, Ni, Pd, Ti, Fe, or Zn compounds can be used as catalysts. Preferably the reaction is performed without any catalyst. The reaction temperature is –80 to 60° C., preferably –20 to 20° C., and the reaction time is from 0.5 to 15 hours, preferably less than 3 hours. The organometallic reagent is used in an amount of from 0.5 to 2.5 equivalents, preferably from 0.8 to 1.8 equivalents, based on the equivalents of the compound of formula III.

After the reaction, the ring closes spontaneously affording citalopram. The resulting citalopram can be isolated as a base or a pharmaceutically acceptable salt thereof.

All the reactions from 5-cyanophthalide to citalopram can be performed in one pot which makes the process convenient and saves costs and labour when no isolation or purification processes of intermediates are needed. Another method is to isolate compound II and then perform the following reactions b) and c) in the same pot without the separation of intermediates.

The compound of formula I may be used as a free base or as a pharmaceutically acceptable acid addition salt thereof. The acid addition salts can be prepared by methods known in the art.

Other features of the invention will become apparent in the course of the following descriptions of exemplary embodiments which are given for illustration of the invention and are not intended to be limiting thereof.

EXAMPLES

Example 1

2-Chloromethyl-4-cyano-benzoyl chloride:

1-Oxo-1,3-dihydro-isobenzofuran-5-carbonitrile (25 g), boron trifluoride etherate (0.8 ml), and benzyl triethyl ammonium chloride (0.72 g) were suspended in thionyl chloride (92 ml) and heated to reflux for 17 hours. Excess thionyl chloride was removed by distillation under nitrogen to give an internal temperature of 95° C., and heating to reflux was continued for another 24 hours. The product was purified by distillation under reduced pressure. Yield: 27.5 g, 92%. Melting point 44–44.5 C. $^1$H NMR (CDCl3, 400 MHz): 4.83 (2H, s), 7.74 (1H, dd, J=1, 8 Hz), 7.89 (1H, d, J=1 Hz), 8.25 (1H, d, J=8 Hz). $^{13}$C NMR (CDCl3, 100 MHz): 42.7, 116.8, 118.0, 132.2, 133.8, 134.0, 135.7, 140.0, 166.9. IR (KBr): ν 3108, 3077, 2963, 2239, 1755, 1604, 1298, 1195, 1103, 944, 935, 840 cm$^{-1}$.

3-Chloromethyl-4-(4-fluoro-benzoyl)-benzonitrile:

A solution of 4-fluoro phenylmagnesium bromide (3.76 g) in tetrahydrofuran (15 ml) was added to a cooled solution of 2-chloromethyl-4-cyano-benzoyl chloride (3.95 g) in tetrahydrofuran (10 ml) so that the temperature did not raise above 0° C. The mixture was warmed slowly to room temperature and stirred over night. Saturated ammonium chloride solution (60 ml) was added and stirring continued for 0.5 hours. The phases were separated and the aqueous phase was extracted with diethylether (30 ml). The combined organic phases were dried over sodium sulfate, filtered and dried in vacuo to give a brown solid. Flash chromatography (ethyl acetate/n-hexane=1/10) provided the product as colourless solid. Yield 2.95 g, 58%. $^1$H NMR (CDCl3, 400 MHz): 4.71 (2H, s), 7.16–7.21 (2H, m), 7.46 (1H, d, J=7.9 Hz), 7.71 (1H, dd, J=1.5, 7.9 Hz), 7.81–7.86 (2H, m), 7.89 (1H, d, J=1.5 Hz). $^{13}$C NMR (CDCl3, 100 MHz): 42.3, 115.0, 116.4, 116.6, 117.9, 129.6, 132.95, 132.98, 133.4, 133.5, 134.3, 138.7, 142.4, 165.5, 168.1, 194.5.

1-(3-Dimethylamino-propyl)-1-(4-fluoro-phenyl)-1,3-dihydro-isobenzofuran-5-carbonitrile:

A solution of freshly prepared 3-dimethylaminopropylmagnesium chloride (0.6M in THF, 7.6 ml) was added to a cooled solution of 3-chloromethyl-4-(4-fluoro-benzoyl)-benzonitrile (0.5 g) in ethylene glycol dimethyl ether (4 ml) so that the temperature did not raise above −4° C. The mixture was stirred for 30 minutes at −15° C. and 100 minutes at room temperature before 0.5N hydrobromic acid was added to adjust the pH to 10. The phases were separated and the aqueous phase was extracted twice with toluene (25 ml). The combined organic phases were dried over sodium sulfate, filtered and dried in vacuo to give a viscous oil (0.44 g, 75%). Spectral and analytical data were in accordance with the literature.

Example 2

2-Chloromethyl-4-cyano-benzoyl Chloride:

1-Oxo-1,3-dihydro-isobenzofuran-5-carbonitrile (80 g), boron trifluoride etherate (4.4 ml), benzyltriethyl ammonium chloride (9.2 g), and thionyl chloride (55 ml) were suspended in xylene (320 ml). The mixture was heated to reflux for 4 hours and volatiles were removed under reduced pressure. The product was purified by distillation under high vacuum. Yield: 78.2 g, 73%. Melting point 44–44.5° C. $^1$H NMR (CDCl3, 400 MHz): 4.83 (2H, s), 7.74 (1H, dd, J=1, 8 Hz), 7.89 (1H, d, J=1 Hz), 8.25 (1H, d, J=8 Hz). $^{13}$C NMR (CDCl3, 100 MHz): 42.7, 116.8, 118.0, 132.2, 133.8, 134.0, 135.7, 140.0, 166.9. IR (KBr): ν 3108, 3077, 2963, 2239, 1755, 1604, 1298, 1195, 1103, 944, 935, 840 cm$^{-1}$.

3-Chloromethyl-4-(4-fluoro-benzoyl)-benzonitrile:

A solution of 4-fluoro phenylmagnesium bromide (0.73M in THF, 170 ml) was added to a cooled solution of 2-chloromethyl-4-cyano-benzoyl chloride (25.0 g) in toluene (200 ml) so that the temperature did not raise above 0° C. The mixture was stirred at 0° C. for 2 hours. An aqueous solution of HCl (250 ml) was added and stirring continued for 0.5 hours. The phases were separated and the aqueous phase was extracted with toluene (200 ml). The combined organic phases were washed with saturated NaHCO$_3$ solution (200 ml) and water (100 ml). The solvents were evaporated in vacuo to give a brownish oil (29.0 g, 90%). Spectral and analytical data were in accordance with the example above.

1-(3-Dimethylamino-propyl)-1-(4-fluoro-phenyl)-1,3-dihydro-isobenzofuran-5-carbonitrile:

A solution of 3-dimethylaminopropylmagnesium chloride (1.2M in THF, 84 ml) was added to a cooled solution of 3-chloromethyl-4-(4-fluoro-benzoyl)-benzonitrile (25.0 g) in a mixture of toluene (175 ml) and THF (50 ml) so that the temperature did not raise above −5° C. The mixture was stirred for 2 hours at 0° C. before water (100 ml) and saturated NH$_4$Cl solution were added to adjust the pH to 9. The phases were separated and the aqueous phase was extracted twice with toluene (200 ml). The combined organic phases were washed with water (200 ml) and concentrated in vacuo to give a viscous oil (28.0 g, 95%). Spectral and analytical data were in accordance with the literature.

Example 3

1-(3-Dimethylamino-propyl)-1-(4-fluoro-phenyl)-1,3-dihydro-isobenzofuran-5-carbonitrile in One Pot 1-Oxo-1,3-dihydro-isobenzofuran-5-carbonitrile (5 g), boron trifluoride etherate (0.2 ml), and benzyl triethyl ammonium chloride (0.36 g) were suspended in thionyl chloride (18 ml) and heated to reflux for 6 hours. Excess thionyl chloride was removed by distillation under nitrogen, and heating to reflux was continued for another 17 hours. Toluene (50 ml) was added, and volatiles (45 ml) were removed by distillation. Dry tetrahydrofuran (25 ml) was added, and 4-fluorophenylmagnesium bromide (6.26 g) in dry tetrahydrofuran (25 ml) was added slowly at −15° C. The reaction mixture was stirred at room temperature for 3 hours and 3-dimethylamino propyl magnesium chloride (4.36 g) in dry tetrahydrofuran (20 ml) was added slowly at −15° C. The reaction mixture was stirred at room temperature over night and heated to reflux for 1 hour. The reaction was quenched with saturated ammonium chloride solution (300 ml), and the phases were separated. The aqueous phase was extracted 3 times with tert-butyl methyl ether (100 ml), and the combined organic phases were washed with brine (100 ml) and dried over sodium sulfate. Filtration and evaporation of volatiles gave a brown oil, which was dissolved in 1N hydrochloric acid (250 ml) and toluene (150 ml). The phases were separated, and the organic phase was washed with 1N hydrochloric acid (100 ml). The combined aqueous phases were treated with concentrated sodium hydroxide solution to obtain a pH of 14. The mixture was extracted 3 times with toluene (100 ml), and the combined organic phases were washed with brine (100 ml) and dried over sodium sulfate. Filtration and evaporation of volatiles gave a brown oil. Yield: 1 g, 10%. Spectral and analytical data were in accordance with the literature.

Example 4

1-(3-Dimethylamino-propyl)-1-(4-fluoro-phenyl)-1,3-dihydro-isobenzofuran-5-carbonitrile:

A solution of 4-fluoro phenylmagnesium bromide (0.7M in THF, 16 ml) was added to a cooled solution of 2-chloromethyl-4-cyano-benzoyl chloride (1.75 g) in toluene (20 ml) so that the temperature did not rise above 0° C. After 40 minutes a solution of 3-dimethylaminopropylmagnesium chloride (0.85M in THF, 10 ml) was added so that the temperature did not rise above 2° C. The mixture was stirred for 30 minutes, and water (30 ml) was added. The pH of the mixture was adjusted to 4.5, and the phases were separated. The pH of the aqueous phase was adjusted to 8 and extracted with toluene (30 ml) and 2-propanol (10 ml). The organic phase was concentrated in vacuo to give a viscous oil (1.5 g, 56%). Spectral and analytical data were in accordance with the literature.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A compound having formula II

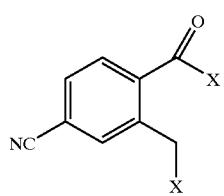

II wherein X is halogen.

2. The compound of claim 1 wherein X is Cl or Br.

3. The compound of claim 1 where X is Cl.

4. A process for preparing a compound of formula I:

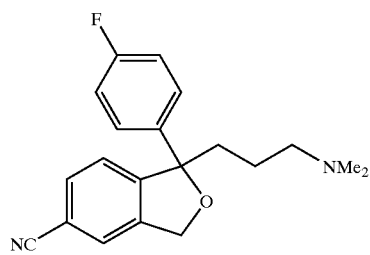

I said process comprising:
(a) reacting a compound of formula III:

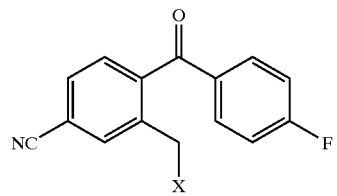

III wherein X is halogen, with an organometallic 3-dimethylaminopropyl halide.

5. The process of claim 4, wherein said organometallic 3-dimethylaminopropyl halide is 3-(N,N-dimethylamino) propylmagnesium chloride.

6. The process of claim 4, wherein X is Cl or Br.

7. The process of claim 4, wherein said compound of formula III is (4-fluorophenyl)-(2-chloromethyl-4-cyanophenyl)methanone.

8. A process for preparing a compound of formula II:

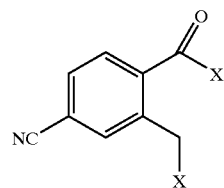

II wherein X is halogen,
said process comprising:
(a) halogenating 5-cyanophthalide.

9. The process of claim 8, wherein X is Cl or Br.

10. The process of claim 8, wherein X is Cl.

* * * * *